United States Patent [19]

Meyer et al.

[11] 4,028,377
[45] June 7, 1977

[54] O,S-DIALKYL- AND O-ALKYL-S-ALKOXYALKYL-S-1,2,4-OXA-DIAZOLYL-3-METHYLENE DITHIOPHOSPHATES

[75] Inventors: Willy Meyer, Riehen; Beat Böhner, Binningen; Dag Dawes, Muttenz; Kurt Rüfenacht, Basel, all of Switzerland

[73] Assignee: Ciba-Geigy Corporation, Ardsley, N.Y.

[22] Filed: Oct. 23, 1974

[21] Appl. No.: 517,359

[30] Foreign Application Priority Data

Nov. 2, 1973 Switzerland .................... 15460/73
Nov. 2, 1973 Switzerland .................... 15461/73
Aug. 16, 1974 Switzerland .................... 11260/74

[52] U.S. Cl. .......................... 260/307 G; 424/200
[51] Int. Cl.² .............................. C07F 9/165
[58] Field of Search .................... 260/307 G

[56] References Cited

UNITED STATES PATENTS

| | | | |
|---|---|---|---|
| 3,432,519 | 3/1969 | Metivier et al. | 260/307 |
| 3,733,379 | 5/1973 | Szabo | 260/950 |
| 3,767,666 | 10/1973 | Zielinski | 260/308 C |
| 3,794,730 | 2/1974 | Szabo | 424/200 |
| 3,821,246 | 6/1974 | Kishino et al. | 260/326 E |
| 3,843,655 | 10/1974 | Baranyovits et al. | 260/256.5 R |
| 3,862,188 | 1/1975 | Milzner et al. | 260/251 P |
| 3,867,397 | 2/1975 | Bohner et al. | 260/308 R |
| 3,876,666 | 4/1975 | Oswald et al. | 260/343.2 P |

OTHER PUBLICATIONS

Wood(I)–C. A. 72, 79062q (1970).
Wood(II)–C. A. 75, 110321m (1971).

*Primary Examiner*—Alton D. Rollins
*Assistant Examiner*—Mark L. Berch
*Attorney, Agent, or Firm*—Frederick H. Rabin

[57] ABSTRACT

1,2,4-Oxadiazoles, their manufacture and use as active ingredients in pesticides especially insecticides and acaricides. The compounds correspond to the formula

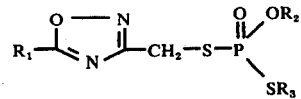

wherein $R_1$ represents hydrogen, unsubstituted alkyl, benzyl or phenyl, $R_2$ represents methyl or ethyl, and $R_3$ represents unsubstituted $C_1$–$C_7$ alkyl optionally interrupted by oxygen or represents $C_3$–$C_4$ alkenyl.

19 Claims, No Drawings

O,S-DIALKYL- AND O-ALKYL-S-ALKOXYALKYL-S-1,2,4-OXA-DIAZO-LYL-3-METHYLENE DITHIOPHOSPHATES

The present invention relates to derivatives of 1,2,4-oxadiazole, to processes for their preparation and to their use in pest control.

The said 1,2,4-oxadiazole derivatives have the formula

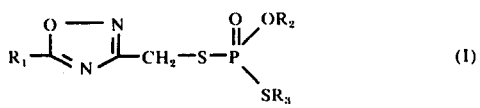

wherein
$R_1$ represents hydrogen, unsubstituted alkyl, benzyl or phenyl,
$R_2$ represents methyl or ethyl, and
$R_3$ represents unsubstituted $C_1$–$C_7$-alkyl optionally interrupted by oxygen, or $C_3$–$C_4$-alkenyl.

The alkyl or alkenyl groups represented by $R_1$ and $R_3$ can be straight-chain or branched-chain, and in the case of $R_1$ they have 1 to 20, preferably 1 to 7 carbon atoms in the chain. Examples of alkyl or alkenyl groups denoted by $R_1$ and $R_3$ are, inter alia: methyl, ethyl, methoxymethyl, methoxyethyl, ethoxyethyl, propyl, isopropyl, n-, i-, sec.-, tert.-butyl, n-pentyl, n-heptyl, n-dodecyl, and isomers thereof, allyl or methallyl.

Compounds of formula I preferred by virtue of their action are those wherein
$R_1$ represents hydrogen, unsubstituted $C_1$–$C_7$-alkyl, benzyl or phenyl,
$R_2$ represents methyl or ethyl, and
$R_3$ represents unsubstituted $C_1$–$C_7$-alkyl optionally interrupted by oxygen, or allyl, Particularly preferred compounds of formula I are those wherein
$R_1$ represents unsubstituted $C_1$–$C_4$-alkyl, benzyl or phenyl,
$R_2$ represents methyl or ethyl, and
$R_3$ represents unsubstituted $C_3$–$C_5$-alkyl optionally interrupted by oxygen.

The compounds of formula I can be prepared by methods known per se, for example, as follows:

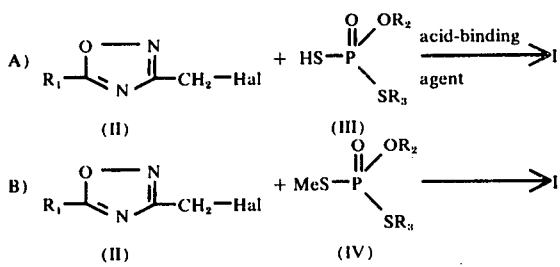

In formulae II, III and IV, the symbols $R_1$, $R_2$ and $R_3$ have the meanings given for formula I, and Hal stands for chlorine or bromine, especially for chlorine, and Me stands for a metal, particularly an alkali metal, ammonium or trialkylammonium.

The processes A and B are performed at a reaction temperature of 0° – 120° C, preferably at 20° – 80° C, at normal pressure and in solvents or diluents. Depending on the reaction conditions, it may be advantageous in order to enhance the yield or reduce the duration of the reaction to add a catalyst, such as copper, copper chloride or potassium iodide. Suitable solvents or diluents are, for example, ethers and ethereal compounds, such as diethyl ether, dipropyl ether, dioxane, dimethoxyethane or tetrahydrofuran, amides such as N,N-dialkylated carboxylic acid amides, aliphatic, aromatic as well as halogenated hydrocarbons, especially benzene, toluene, xylenes, chloroform and chlorobenzene, nitriles such as acetonitrile, dimethylsuphate, ketones such as acetone or methyl ethyl ketone, water, and alcohols such as methanol or ethanol.

Suitable acid-binding agents are: tertiary amines, e.g. trialkylamines, pyridine or dialkylanilines; inorganic bases such as hydrides or hydroxides; carbonates and bicarbonates of alkali metals and alkaline-earth metals.

Starting materials of formulae II, III and IV are known or can be prepared by methods analogous to known methods. For the preparation of compounds of formula I according to methods A and B, it is possible to react, for example, any one of the following starting materials of formula II:

3-chloromethyl-1,2,4-oxadiazole,
3-chloromethyl-5-methyl-1,2,4-oxadiazole,
3-chloromethyl-5-ethyl-1,2,4-oxadiazole,
3-chloromethyl-5-n-propyl-1,2,4-oxadiazole,
3-chloromethyl-5-i-propyl-1,2,4-oxadiazole,
3-chloromethyl-5-n-butyl-1,2,4-oxadiazole,
3-chloromethyl-5-i-butyl-1,2,4-oxadiazole,
3-chloromethyl-5-sec.-butyl-1,2,4-oxadiazole,
3-chloromethyl-5-tert.-butyl-1,2,4-oxadizole,
3-chloromethyl-5-n-pentyl-1,2,4-oxadiazole,
3-chloromethyl-5-n-hexyl-1,2,4-oxadiazole,
3-chloromethyl-5-phenyl-1,2,4-oxadiazole with any one of the following examples of starting materials of formula III or salts thereof of formula IV:

S-n-propyl-O-ethyl-dithiophosphoric acid,
S-ethyl-O-ethyl-dithiophosphoric acid,
S-i-propyl-O-ethyl-dithiophosphoric acid,
S-n-butyl-O-ethyl-dithiophosphoric acid,
S-i-butyl-O-ethyl-dithiophosphoric acid,
S-sec.-butyl-O-ethyl-dithiophosphoric acid,
S-n-pentyl-O-ethyl-dithiophosphoric acid,
S-methyl-O-ethyl-dithiophosphoric acid,
S-(2-methoxyethyl)-O-ethyl-dithiophosphoric acid,
S-(2-ethoxyethyl)-O-ethyl-dithiophosphoric acid,
S-n-hexyl-O-ethyl-dithiophosphoric acid,
S-n-heptyl-O-ethyl-dithiophosphoric acid,
S-n-propyl-O-methyl-dithiophosphoric acid,
S-n-butyl-O-methyl-dithiophosphoric acid,
S-i-butyl-O-methyl-dithiophosphoric acid,
S-sec.-butyl-O-methyl-dithiophosphoric acid,
S-n-pentyl-O-methyl-dithiophosphoric acid,
S-(2-methoxyethyl)-O-methyl-dithiophosphoric acid,
S-(2-ethoxyethyl)-O-methyl-dithiophosphoric acid,
S-allyl-O-ethyl-dithiophosphoric acid ester,
S-methallyl-O-ethyl-dithiophosphoric acid ester, The active substances of formula I are suitable for the control of various animal and plant pests. They thus possess nematocidal properties, and can be used, for example, for the control of phytopathogenic nematodes. In some cases, the active substances of formula I are suitable as herbicides and as agents regulating plant growth, and also as agents for the control of viruses, bacteria and phytopathogenic fungi. They are effective in particular, however, against all development stages, such as eggs, larvae, nymphs, pupae and adults, of insects and members of the order acarina, such as mites and ticks.

The compounds of formula I have a lethal or repellant action against, for example, the following insects or members of the order acarina:- insects of the families: *Tettigonidae, Gryllidae, Gryllotalpidae, Blattidae, Reduviidae, Phyrrhocoridae, Cimicidae, Delphacidae, Aphididae, Diaspididae, Pseudococidae, Scarabaeidae, Dermestidae, Coccinellidae, Tenebrionidae, Chrysomelidae, Bruchidae, Tineidae, Noctuidae, Lymtriidae, Pyralidae, Gulicidae, Tipulidae, Stomoxydae, Trypetidae, Muscidae, Galliphoridae* and *Pulicidae;* as well as acarids of the families: *Ixodidae, Argasidae, Tetranychidae* and *Dermanyssidae*.

The insecticidal and/or acaricidal action can be substantially broadened and adapted to suit given conditions by the addition of other insecticides and/or acaricides. Suitable additives are, for example:
  organic phosphorus compounds,
  nitrophenols and derivatives thereof, formamidines, ureas,
  carbamates and chlorinated hydrocarbons.

Surprisingly, compounds of formula I are clearly more effective against cotton pests, such as Spodoptera littoralis and Heliothis virescens larvae $L_3$, than analogous compounds known from the British Patent Specification No. 1,213,707.

The compounds of formula I can be used on their own or together with suitable carriers and/or additives. Suitable carriers and additives may be solid or liquid, and they correspond to the substances common in formulation practice, such as, e.g. natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice. Also to be mentioned are cattle dips and spray races, in which aqueous preparations are used.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:
solid preparations: dusts, scattering agents, granulates, coated granulates, impregnated granulates and homogeneous granulates;
liquid preparations:
  a. water-dispersible active-substance concentrates: wettable powders, pastes or emulsions;
  b. solutions.

The content of active substance in the described agents is between 0.1 and 95%.

The active substances of formula I can be formulated, for example, as follows:
Dusts:
The following substances are used in the preparation of (a) a 5% dust, and (b) a 2% dust:
  a. 5 parts of active substance, 95 parts of talcum;
  b. 2 parts of active substance, 1 part of highly dispersed silicic acid, 97 parts of talcum.

The active substances are mixed and ground with the carriers.
Granulate:
The following substances are used to prepare a 5% granulate:

| | |
|---|---|
| 5 | parts of active substance, |
| 0.25 | part of epichlorohydrin, |
| 0.25 | part of cetyl polyglycol ether, |
| 3.50 | parts of polyethylene glycol, |
| 91 | parts of kaolin (particle size 0.3 – 0.8 mm). |

The active substance is mixed with epichlorohydrin and dissolved with 6 parts of actone; the polyethylene glycol and cetyl polyglycol ether are then added. The solution thus obtained is sprayed onto kaolin, and the acetone is subsequently evaporated off in vacuo.
Wettable powder:
The following constituents are used for the preparation of (a) a 40%, (b) and (c) a 25%, and (d) a 10% wettable powder:

| | | |
|---|---|---|
| a) | 40 | parts of active substance, |
| | 5 | parts of sodium lignin sulphonate, |
| | 1 | part of sodium dibutyl-naphthalene sulphonate, |
| | 54 | parts of silicic acid; |
| b) | 25 | parts of active substance, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |
| | 19.5 | parts of silicic acid, |
| | 19.5 | parts of Champagne chalk, |
| | 28.1 | parts of kaolin; |
| c) | 25 | parts of active substance, |
| | 2.5 | parts of isooctylphenoxy-polyoxyethylene-ethanol, |
| | 1.7 | parts of Champagne chalk/hydroxyethyl cellulose mixture (1:1), |
| | 8.3 | parts of sodium aluminium silicate, |
| | 16.5 | parts of kieselguhr, |
| | 46 | parts of kaolin; |
| d) | 10 | parts of active substance, |
| | 3 | parts of a mixture of the sodium salts of saturated fatty alcohol sulphates, |
| | 5 | parts of naphthalenesulphonic acid/formaldehyde condensate, |
| | 82 | parts of kaolin. |

The active substances are intimately mixed, in suitable mixers, with the additives, the mixture being then ground in the appropriate mills and rollers. Wettable powders are obtained which can be diluted with water to give suspensions of any desired concentration.
Emulsifiable concentrates:
The following substances are used to prepare (a) a 10% and (b) a 25% emulsifiable concentrate:

| | | |
|---|---|---|
| a) | 10 | parts of active substance, |
| | 3.4 | parts of epoxidised vegetable oil, |
| | 3.4 | parts of a combination emulsifier consisting of fatty alcohol polyglycol ether and alkyl-arylsulphonate calcium salt, |
| | 40 | parts of dimethylformamide, |
| | 43.2 | parts of xylene; |
| b) | 25 | parts of active substance, |
| | 2.5 | parts of epoxidised vegetable oil, |
| | 10 | parts of an alkylarylsulphonate/fatty alcohol polyglycol ether mixture, |
| | 5 | parts of dimethylformamide, |
| | 57.5 | parts of xylene. |

From these concentrates it is possible to prepare, by dilution with water, emulsions of any desired concentration.

Spray:

The following constituents are used to prepare a 5% and 95% spray, respectively:

| | |
|---|---|
| 5 | parts of active substance, |
| 1 | part of epichlorhydrin, |
| 94 | parts of ligroin (boiling limits 160 – 190° C); and |
| 95 | parts of active substance, |
| 5 | parts of epichlorohydrin. |

EXAMPLE 1

Preparation of O-ethyl-S-(n)propyl-S-[5-methyl-1,2,4-oxadiazole-methylene(3)]-dithiophosphate.

9.3 g of 3-chloromethyl-5-methyl-1,2,4-oxadiazole in 20 ml of methanol is added dropwise at 40° C to a solution of 20 g of potassium-O-ethyl-S-(n)propyl-dithiophosphate and 70 ml of methanol. The solution is stirred for 2 hours at the reflux temperature.

The resulting suspension is cooled to 20° C and 200 ml of methylene chloride is added; the whole is extracted with water three times, dried with sodium sulphate and concentrated by evaporation. There is obtained the compound of the formula $$CH_3 \underset{N}{\overset{O-N}{\diagup\!\!\diagdown}} CH_2-S-\overset{O}{\underset{OC_2H_5}{\overset{\|}{P}}} \diagup S-C_3H_{7(n)}$$

having a refractive index of $n_D^{22} = 1.5129$.

The following compounds are obtained in an analogous manner:

$$R_1 \underset{N}{\overset{O-N}{\diagup\!\!\diagdown}} CH_2-S-\overset{O}{\underset{SR_3}{\overset{\|}{P}}} \diagup OR_2$$

| $R_1$ | $R_2$ | $R_3$ | Physical data |
|---|---|---|---|
| —CH$_3$ | —C$_2$H$_5$ | —C$_3$H$_{7(i)}$ | $n_D^{23}$ = 1,5190 |
| —CH$_3$ | —C$_2$H$_5$ | —C$_4$H$_{9(n)}$ | $n_D^{21}$ = 1,5084 |
| —CH$_3$ | —C$_2$H$_5$ | —C$_4$H$_{9(i)}$ | $n_D^{22}$ = 1,5171 |
| —CH$_3$ | —C$_2$H$_5$ | —C$_4$H$_{9(sec.)}$ | $n_D^{23.5}$ = 1,5198 |
| —C$_3$H$_5$ | —C$_2$H$_5$ | —C$_3$H$_{7(n)}$ | $n_D^{24}$ = 1,5188 |
| —C$_3$H$_{7(i)}$ | —C$_2$H$_5$ | —C$_3$H$_{7(n)}$ | $n_D^{23}$ = 1,5145 |
| | —C$_2$H$_5$ | —C$_3$H$_{7(n)}$ | $n_D^{22}$ = 1,5522 |
| —CH$_2$—⌬ | | | |
| —CH$_3$ | —C$_2$H$_5$ | —CH$_2$CH$_2$OCH$_3$ | $n_D^{24}$ = 1,5217 |
| —CH$_3$ | —C$_2$H$_5$ | —C$_5$H$_{11(n)}$ | $n_D^{23.5}$ = 1,5132 |
| —C$_3$H$_{7(i)}$ | —C$_2$H$_5$ | —C$_4$H$_{9(sec.)}$ | $n_D^{23}$ = 1,511 |
| —CH$_3$ | —C$_2$H$_5$ | —CH$_2$—CH=CH$_2$ | $n_D^{23}$ = 1,5365 |
| —CH$_3$ | —CH$_3$ | —C$_3$H$_{7(n)}$ | $n_D^{26}$ = 1,5280 |
| —C$_4$H$_{9(tert.)}$ | —C$_2$H$_5$ | —C$_3$H$_{7(n)}$ | $n_D^{23}$ = 1,5095 |
| —C$_3$H$_{7(n)}$ | —C$_2$H$_5$ | —C$_3$H$_{7(n)}$ | $n_D^{23}$ = 1,5136 |
| —⌬ | —C$_2$H$_5$ | —C$_3$H$_{7(n)}$ | $n_D^{23}$ = 1,5732 |
| —⌬ | —C$_2$H$_5$ | —C$_4$H$_{9(sec.)}$ | $n_D^{28}$ = 1,5582 |
| —⌬ | —C$_2$H$_5$ | —C$_4$H$_{9(n)}$ | $n_D^{24}$ = 1,5626 |
| —⌬ | —C$_2$H$_5$ | —CH$_2$CH$_2$OCH$_3$ | $n_D^{24}$ = 1,5707 |

EXAMPLE 2

A. Insecticidal stomach poison action

Cotton plants were sprayed with a 0.05% aqueous active-substance emulsion (obtained from a 10% emulsifiable concentrate).

After the drying of the resulting coating, *Spodoptera littoralis* or *Heliothis virescens* larvae L$_3$ were placed onto the cotton plants. The test was carried out at 24° C with 60% relative humidity.

Compounds according to Example 1 exhibited in the above test a good insecticidal stomach poison action against the larvae of *Spodoptera littoralis* and *Heliothis virescens*.

B. Systemic insecticidal action

In order to determine the systemic action, rooted bean plants (*Vicia faba*) were placed into a 0.01% aqueous active-substance solution (obtained from a 10% emulsifiable concentrate). After a period of 24 hours, bean aphids (*Aphis fabae*) were placed onto the parts of the plant above the soil. The insects were protected by a special device from the effects of contact and of gas. The test was performed at 24° C with 70% relative humidity.

Compounds according to Example 1 exhibited in the above test a systemic action against *Aphis fabae*.

EXAMPLE 3

Action against ticks

A. *Rhipicephalus bursa*

In each case, 5 adult ticks or 50 tick larvae were placed into a small glass test tube, and subsequently immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks, and in the case of the larvae after 2 days. There were two repeats for each test.

B. *Boophilus microplus* (larvae)

With a dilution series analogous to that in Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 4

Acaricidal action

*Phaseolus vulgaris* (plants) were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no running-off of the spray liquor. As assessment was made after 2 to 7 days, by examination under a binocular, of the living and of the dead larvae, adults and eggs, and the results were expressed as percentages. The treated plants were kept during the "holding time" in greenhouse compartments at 25° C.

Compounds according to Example 1 were effective in the above test against adults, larvae and eggs of *Tetranychus urticae*.

EXAMPLE 5

Action against soil nematodes

In order to test the action against soil nematodes, the active substances were added, in the concentration stated in each case, to soil infested with root-gall-nematodes (*Meloidogyne arenaria*); the whole was then intimately mixed. In the one test series, tomato seedlings were planted immediately after preparation of the soil in this manner, and in the other test series tomatoes were planted after a waiting time of 8 days.

For an assessment of the nematocidal action, the galls present on the roots were counted 28 days after planting and sowing, respectively.

Active substances according to Example 1 exhibited in this test a good action against *Meloidogyne arenaria*.

What we claim is:

1. A compound of the formula

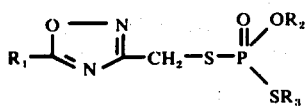

wherein
R₁ represents unsubstituted $C_1$–$C_4$-alkyl, benzyl or phenyl,
R₂ represents methyl or ethyl, and
R₃ represents unsubstituted $C_3$–$C_5$-alkyl optionally interrupted by oxygen.

2. O-Ethyl-S-(n)butyl-S-(5-phenyl-1,2,4-oxadiazole-methylene (3) )-dithiophosphate according to claim 1.
3. O-Ethyl-S-2-methoxyethyl-S-(5-methyl-1,2,4-oxadiazole-methylene (3) )-dithiophosphate according to claim 1.
4. O-Ethyl-S-(n)propyl-S-(5-methyl-1,2,4-oxadiazole-methylene (3) )-dithiophosphate according to claim 1.
5. O-Ethyl-S-(n)propyl-S-(5-isopropyl-1,2,4-oxadiazole-methylene (3) )-dithiophosphate according to claim 1.
6. O-Ethyl-S-(sec)butyl-S-(5-isopropyl-1,2,4-oxadiazole-methylene (3) )-dithiophosphate according to claim 1.
7. O-Ethyl-S-(sec)butyl-S-(5-methyl-1,2,4-oxadiazole-methylene (3) )-dithiophosphate according to claim 1.
8. O-Ethyl-S-(n)pentyl-S-(5-methyl-1,2,4-oxadiazole-methylene (3) )-dithiophosphate according to claim 1.
9. O-Ethyl-S-2-methoxyethyl-S-(5-methyl-1,2,4-oxadiazole-methylene (3) )-dithiophosphate according to claim 1.
10. O-Ethyl-S-allyl-S-(5-methyl-1,2,4-oxadiazole-methylene (3) )-dithiophosphate.
11. O-Ethyl-S-(n)propyl-S-(5-ethyl-1,2,4-oxadiazole-methylene (3) )-dithiophosphate according to claim 1.
12. O-Ethyl-S-(i)butyl-S-(5-methyl-1,2,4-oxadiazole-methylene (3) )-dithiophosphate according to claim 1.
13. O-Methyl-S-(n)propyl-S-(5-methyl-1,2,4-oxadiazole-methylene (3) )-dithiophosphate according to claim 1.
14. O-Ethyl-S-(n)propyl-S-(5-tert.butyl-1,2,4-oxadiazole-methylene (3) )-dithiophosphate according to claim 1.
15. O-Ethyl-S-(n)propyl-S-(5-benzyl-1,2,4-oxadiazole-methylene (3) )-dithiophosphate according to claim 1.
16. O-Ethyl-S-(n)propyl-S-(5-(n)propyl-1,2,4-oxadiazole-methylene (3) )-dithiophosphate according to claim 1.
17. O-Ethyl-S-(i)propyl-S-(5-methyl-1,2,4-oxadiazole-methylene (3) )-dithiophosphate according to claim 1.
18. O-Ethyl-S-(n)butyl-S-(5-methyl-1,2,4-oxadiazole-methylene (3) )-dithiophosphate according to claim 1.
19. O-Ethyl-S-(sec.)butyl-S-(5-phenyl-1,2,4-oxadiazole-methylene (3) )-dithiophosphate according to claim 1.

* * * * *